United States Patent
Dusci

(10) Patent No.: US 10,966,990 B2
(45) Date of Patent: Apr. 6, 2021

(54) MIDAZOLAM IN FLEXIBLE BAGS

(71) Applicant: InfoRLife SA, Campascio (CH)

(72) Inventor: Sergio Dusci, Tresivio (IT)

(73) Assignee: InfoRLife SA, Campascio (CH)

( * ) Notice: Subject to any disclaimer, the term of this patent is extended or adjusted under 35 U.S.C. 154(b) by 0 days.

(21) Appl. No.: 16/013,722

(22) Filed: Jun. 20, 2018

(65) Prior Publication Data

US 2019/0388432 A1 Dec. 26, 2019

(51) Int. Cl.
*A61K 31/5517* (2006.01)
*A61K 47/02* (2006.01)
*A61K 9/08* (2006.01)
*A61K 9/00* (2006.01)

(52) U.S. Cl.
CPC ........ *A61K 31/5517* (2013.01); *A61K 9/0019* (2013.01); *A61K 9/08* (2013.01); *A61K 47/02* (2013.01)

(58) Field of Classification Search
CPC ......... A61K 31/137; A61K 9/08; A61K 47/02
See application file for complete search history.

(56) References Cited

U.S. PATENT DOCUMENTS 5,443,883 A * 8/1995 Park .......................... B32B 5/12
  428/103
9,649,296 B1 * 5/2017 Pizza ...................... A61J 1/065

OTHER PUBLICATIONS

Hypnovel® Product Information by Roche, Oct. 2007 (Year: 2007).*
Patient Information Leaflet, accord, Dec. 2014 (Year: 2014).*
Bakan et al. Rev Bras Anestesiol. 2013;63(4):362-365 (Year: 2013).*
Dr. Amita Fotedar, Difference between Ampoule and Vial, May 1, 2018 (Year: 2018).*
ISMP., ISMP Safe Practice Guidelines for Adult IV Push Medications, 2015. (Year: 2015).*

* cited by examiner

*Primary Examiner* — Jean P Cornet
(74) *Attorney, Agent, or Firm* — Oblon, McClelland, Maier & Neustadt, L.L.P.

(57) ABSTRACT

Terminally sterilized, preservative-free aqueous midazolam solution comprising 0.25 to 1.5 mg/ml of midazolam, a tonicity adjusting agent to provide an osmolality of from 260 and 320 mosm/kg and sufficient acid and optionally a base to provide a pH of from about 2.5 to 3.5 with the remainder water for injection packaged in a flexible plastic container.

13 Claims, 2 Drawing Sheets

Months

MIDAZOLAM IN FLEXIBLE BAGS

FIELD OF THE INVENTION

This invention relates to ready-to-use midazolam intravenous solutions in flexible plastic bags.

BACKGROUND OF THE INVENTION

Midazolam is a short-acting benzodiazepine central nervous system (CNS) depressant. Midazolam is administered either intramuscularly (IM) or intravenously (IV). Midazolam is provided in glass vials or ampules at concentrations 1 mg/ml and 5 mg/ml having volumes of 1 ml, 2 ml, and 5 ml. For IV administration it is necessary to introduce the midazolam into an IV bag containing a suitable IV solution. When the solution is isotonic saline, the bag can be stored overnight at room temperature, other IV solutions such midazolam in lactate Ringer's solution have a useful life of only 4 hours. Further, if the entire vial is not used, the vial must be disposed of as the vials are single use only.

Midazolam is used intramuscularly or intravenously for preoperative sedation/anxiolysis/amnesia; intravenously as an agent for sedation/anxiolysis/amnesia prior to or during diagnostic, therapeutic or endoscopic procedures, such as bronchoscopy, gastroscopy, cystoscopy, coronary angiography, cardiac catheterization, oncology procedures, radiologic procedures, suture of lacerations and other procedures either alone or in combination with other CNS depressants Midazolam is also used intravenously for induction of general anesthesia, before administration of other anesthetic agents. With the use of narcotic premedication, induction of anesthesia can be attained within a relatively narrow dose range and in a short period of time. Intravenous midazolam can also be used as a component of intravenous supplementation of nitrous oxide and oxygen (balanced anesthesia). Midazolam is also used for continuous intravenous infusion for sedation of intubated and mechanically ventilated patients as a component of anesthesia or during treatment in a critical care setting.

With the current sources of midazolam packaged in vials or ampules the hospital of clinic must prepare its own IV bags. Ready-to-infuse products offer convenience and value to the medical profession because they do not require dilution. Furthermore, by eliminating the need to perform manual admixtures, medication errors related to admixing are reduced. Additionally, terminally sterilized product packaged in IV infusion bags provide greater assurance of sterility and lack of microbial contamination, as they do not require any handling before administration. Hospitals and clinics prefer bags because of ease of storage and less risk of breakage. Ready-to-infuse bags also avoid dilution errors which in the case of midazolam can have serious consequences since an overdose may lead to death.

There currently are no ready-to-use midazolam IV bags available. Accordingly there is a need for a midazolam IV bag which has a long shelf-life at room temperature. Preferably the shelf-life at room temperature will equal or exceed 24 months at room temperature.

BRIEF SUMMARY OF THE INVENTION

The present invention is directed to ready-to-use midazolam IV solutions in flexible plastic bags. Ready-to-use bags eliminate the need for the hospital pharmacy to predict the number of IV bags it will need each have them ready when needed. If the pharmacy overestimates the need, the bags must be disposed of because their short shelf-life. Making up too few can leave the hospital short of the needed medication. Neither is an optimum situation. The midazolam IV solution in the ready-use-bags allows for the midazolam to be stored near where it will be used simplifying its use and keeping it available where it may be needed on short notice.

BRIEF DESCRIPTION OF THE DRAWINGS

Drawing

Drawing FIG. 1 shows the amount of degradation products as function of time over the six month stability period at 40° C.

Figure 1:
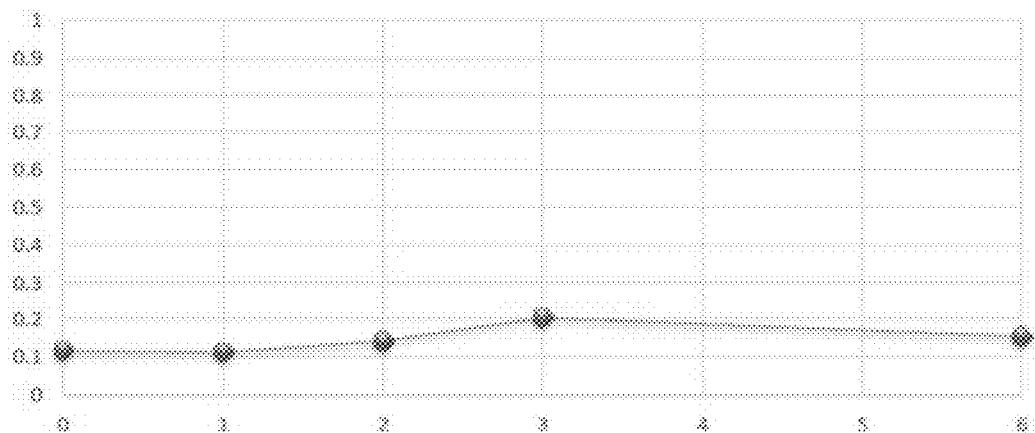
FIGS. 1 to 4 show the properties of a 1 mg/ml product after terminal sterilization and during the six month accelerated stability testing.
Figure 2:
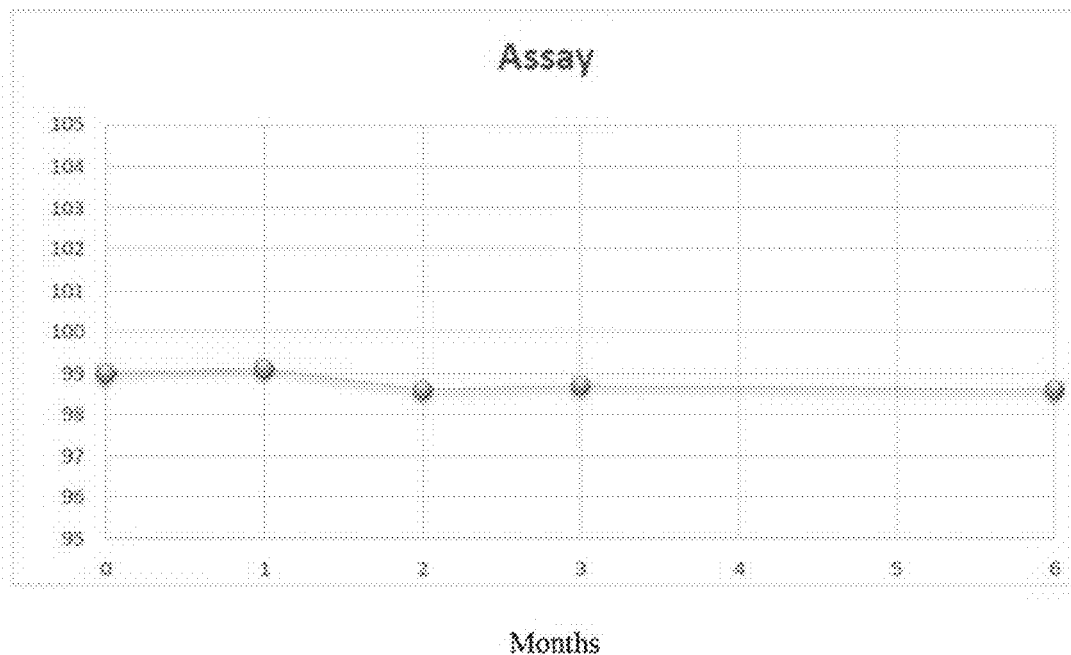

Drawing FIG. 2 reports the amount of midazolam present in the product as a function of time over the stability test.

Figure 3:
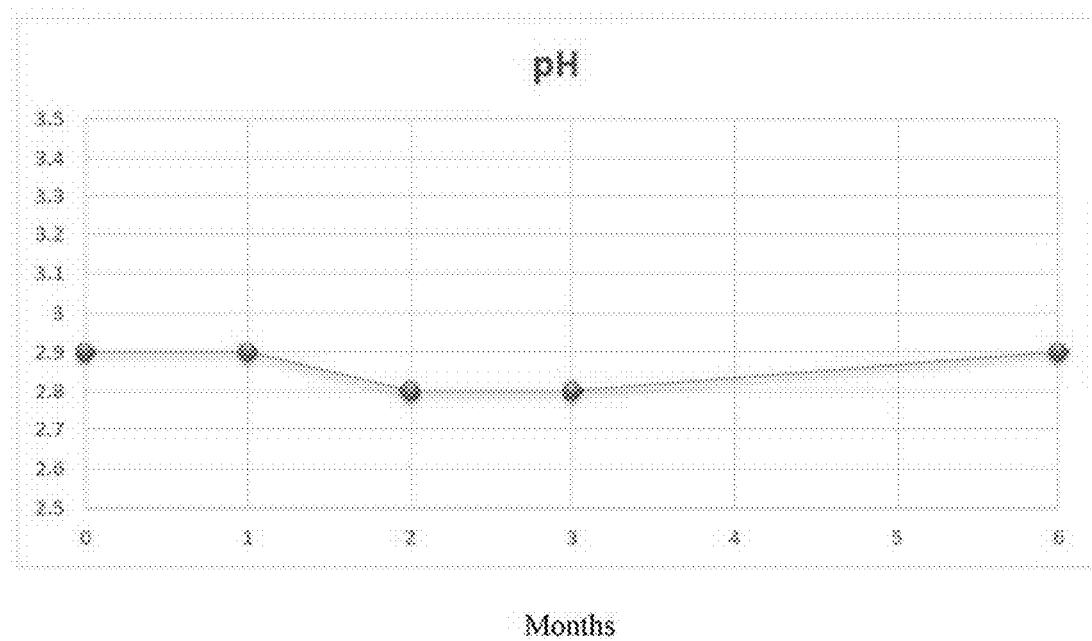

Drawing FIG. 3 reports the change in pH over the course of the stability testing.

Figure 4:
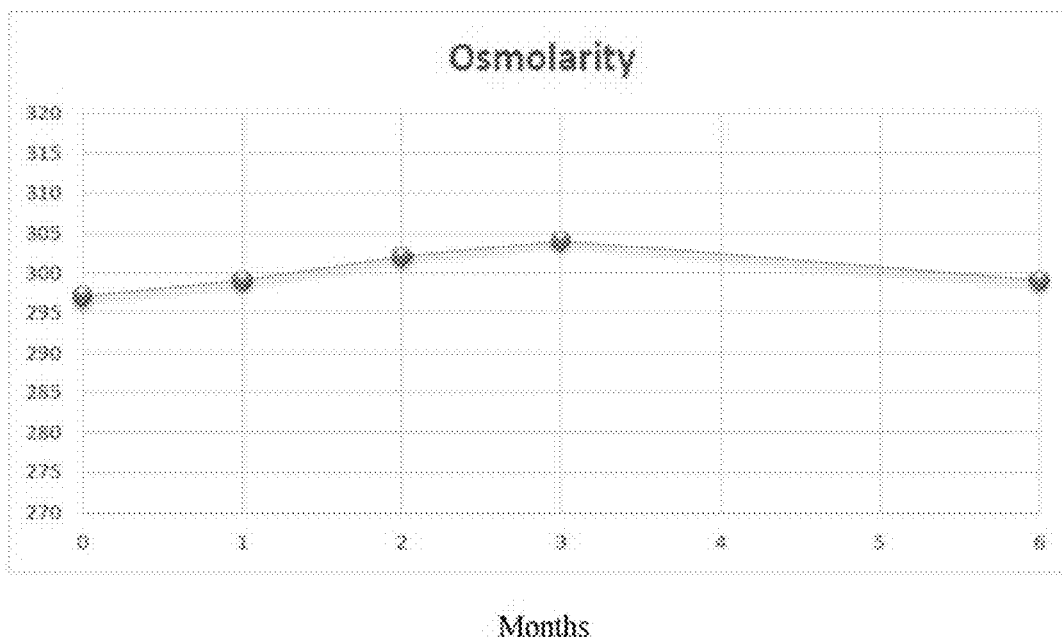

Drawing FIG. 4 shows the variation of osmolarity over the course of the stability test.

DETAILED DESCRIPTION OF THE INVENTION

Vials of midazolam are commonly available at concentrations of 1 mg/ml and 5 mg/ml in volumes of from 2 ml to about 15 ml, most commonly in the United States in 2 ml and 5 ml vials for the 1 mg/ml concentration and 1 ml and 2 ml vials for the 5 mg/ml concentration. For IV administration the contents of the vial must be transferred to an IV bag containing a suitable IV fluid. Suitable IV fluids include saline, 5% dextrose, Ringer's lactate solution, and other IV solutions compatible with midazolam. The formulations of the current invention will contain from about 0.25 mg/ml up to about 1.5 mg/ml, more preferable about 0.5 mg/ml up to about 1.25 mg/ml. Most preferably the formulation will contain from about 0.5 mg/ml to about 1.0 ml/mg. The most preferred concentration is about 1.0 mg/ml or about 0.5 mg/ml. The concentration is chosen to allow the midazolam to administered at a rate consistent the patient's needs. Too low a concentration will require a faster infusion time and too high a concentration can lead to difficulty in controlling the infusion to achieve the desired dosing.

The formulation includes in addition to the midazolam, a tonicity adjusting agent in an amount sufficient to make the solution isotonic. A solution is considered to be isotonic if it has an osmolality of between about 260 and 320 mosm/kg. Suitable isotonic adjusting agents include sodium chloride, potassium chloride and calcium chloride or mixture a thereof. Sodium chloride is the preferred tonicity agent. The amount of the tonicity agent used is sufficient to render the solution isotonic. If sodium chloride is the tonicity adjusting agent and the midazolam concentration is about 1.0 mg/ml, the amount of sodium chloride to be included in the formulation is about 9 mg per mg/ml of the midazolam solution. For a 50 ml solution at a midazolam concentration of 1 mg/ml, the amount of sodium chloride is about 450 mg and for a 100 ml solution at a midazolam concentration of 1 mg/ml, the amount of sodium chloride is about 900 mg. The amount of the tonicity agent may be adjusted to achieve the desired mosm/kg.

The solubility of midazolam is less than 0.1 mg/mL at neutral pH and it increases considerably in acidic media. A solubility study has been performed to evaluate the use of midazolam base in the proposed formulation. Since the solubility of midazolam is pH-dependent, the purpose of this study was to evaluate the pH value at which midazolam becomes soluble in aqueous solution. Midazolam at a concentration of 2 mg/mL is soluble in a solution of 0.9% NaCl when the pH reaches a value of about 3.2 pH. The solubility increases at lower pHs. The desired pH of the formulation is about from about 2.5 to about 3.5, preferably 2.8 to 3.2 and more preferably about pH 3. Sufficient acid is added to the solution to achieve the desired pH. Any pharmaceutically acid may be used. Preferably the acid is a pharmaceutically acceptable mineral acid, most preferably hydrochloric acid. If necessary a pharmaceutically acceptable base may be used to raise the pH if needed. The preferred bases are pharmaceutically acceptable inorganic bases such as sodium hydroxide and potassium hydroxide. Sodium hydroxide is the preferred base.

Sufficient water is present to provide the desired midazolam concentration in the final formulation. The formulation does not contain any preservatives. The formulation consists essentially of the midazolam, water, acid, base, if needed, and tonicity agent. In a preferred embodiment, the formulation consists of midazolam, water, acid, base, if needed, and tonicity agent.

The flexible plastic container must be one which is compatible with midazolam. It must also be able to undergo heat sterilization in moist steam. Suitable flexible plastic containers are those made of copolymerized ethylene and vinyl acetate. Preferably the bag is laminated with the inner most layer comprising copolymerized ethylene and vinyl acetate. More preferably the bag comprises from 3 to 7 layers. These materials are commercially available under the tradename Nexcel® by Sealed Air. The volume of the bag is dependent on the volume of premixed formula. The volume of premixed formula can be from 10 ml to 1000 ml, preferable 50 ml and 100 ml based on current midazolam dosing. Larger or smaller volumes can be used depending on dosing requirements. CR3 elastomer copolyester ether bags may also be used for formulations to be sterilized in moist steam provided but are not preferred.

In an embodiment of the present invention, provided are a flexible plastic container with modified ports and closure system suitable for storing midazolam formulations of the present invention which is subjected to typically product sterilization by steam sterilization (e.g., autoclaving, 121° C. for about 20 minutes) without altering the thermal properties of the film layers, ports and closure system as well as maintaining the integrity container. The primary polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer etc. In addition to plastic bags, CZ resin containers, polypropylene and similar resins can be used as rigid containers and syringes.

The ports and the closure system preferably uses commerciality available polymers, elastomers etc. In an exemplary embodiment of the present invention, the administrative and additive ports can be made off external coextruded layer consists of synthetic thermoplastic rubber (Raumedic SRT320) ranging from about 20 to 30% based on an elastomer modified polypropylene. While the internal coextruded layer (PE770) of not more that 50% in composition consists of ethylene vinyl acetate without any further additives (EVA). The tubing ports can be made of two-layer materials, which can withstand both terminal sterilization and co-solvent matrix. Furthermore, the twist-off compositions can be made of polyproplene Granuflex® 4489 between 70-80% and Granuflex® 4371 15-20%. Alternatively the port tube may be a bilayer tube comprising an outer layer of polypropylene and an inner layer of EVA and the twist off made of LDPE and PP. However, other polymers stable, low leachables, and without physical deformation during heat sterilization may also be used for the ports and closure assemblies.

Commercially available flexible plastic containers (bags) such as Excel® (Braun Company) comprising a three-layered ethylene-polypropylene bag having polyester elastomer outer layer, Visiv® (Hospira), Nexcel® (Sealed Air), Intervia® (Baxter) preferably with a non-DEHP fluid path, Technoflex polyolefin bags, etc., for pharmaceutical formulation or medical liquids are assembled of different plastic materials of different properties, thermal resistance and funictionalities. They are typically designed and tested mostly for aqueous formulations admixtures, premixed or ready-to-use pharmaceutical products. Still the combination of the water and drug composition subjected to further heat sterilization can adversely affect plastic materials, sealing integrity and the solutions contained therein unless they are maintained at certain conditions. Thus, the plastic container should be checked after sterilization for integrity before using it for the formulation. In addition, the formulation after sterilization should be analyzed for the presence of substances leached from the container as a result of the sterilization cycle.

In another alternative embodiment, provided are a flexible plastic container with modified ports and closure system suitable for storing the formulations of the present invention which is subjected to typically product sterilization by steam sterilization (e.g., autoclaving, 121° C. for about 15 to 20 minutes) without altering the thermal properties of the film layers, ports and closure system as well as maintaining the integrity container. The primary polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer etc.

Sterilization is accomplished by heat sterilization. Heat sterilization is normally performed using steam, preferably wet steam, or superheated water. The time period for the sterilization must be long enough to meet the sterility requirements required of an injectable product. When steam is used the period may be from about 5 to 30 minutes at temperatures of about 110° C. to 130° C., or from about 10 to 30 minutes at temperatures of about 110° C. to 130° C., preferably at 120° C. to 125° C. for 15 to 30 minutes. In another embodiment, the sterilization can be at 120° C. for 15 to 20 minutes.

Having generally described this invention, a further understanding can be obtained by reference to certain specific examples, which are provided herein for purposes of illustration only, and are not intended to be limiting unless otherwise specified.

Examples

The following solution was prepared and tested.

TABLE 1 composition

| Active Substance(s) | Quantity per Unit (mg/mL) | Function | Reference to standard |
|---|---|---|---|
| Midazolam injection, USP 1 mg/mL | | | |
| Midazolam Base | 1 | API | USP |
| Excipient(s) | | | |
| Sodium Chloride | 9 | Tonicity agent | USP |
| Hydrochloric acid | q.s* | Solubilizing agent/pH adjuster | NF |
| Sodium Hydroxide | q.s to pH | pH adjuster | NF |
| Water for injection | q.s to 1 mL | Solvent | USP |

*Using during dissolution for in situ conversion of Midazolam Base into Midazolam hydrochloride and pH adjustment to pH 3.0.

The tank is filled with about 90% of the target weight of WFI and the solution is cooled to a temperature between 85-70° C. Before the initial weight is reached, starts the recirculation for cooling the solution (<85° C.). The raw materials are added into the tri-blender in the following order: Hydrochloric Acid 37% (to dissolve the API), Midazolam, Sodium chloride. Add Water for Injection to the final weight.
The quantity of material to be used for batch will be the following:

| Proposed Ingredient | Amount mg/mL | Quantity for Batch |
|---|---|---|
| Midazolam Base* | 1 mg | 82 g |
| Sodium chloride | 9 mg | 738 g |
| Hydrochloric Acid | q.s. to pH | q.s. to pH |
| Sodium Hydroxide | q.s. to pH | q.s. to pH |
| Water for Injection, | q.s. to ~1 mL | q.s. to ~82 L |
| Total | | ~82 L |

Adjust the pH to 2.9-3.1 by the addition of Hydrochloric acid 37% diluted in WFI to a concentration of about 1 N. The minimum solution recirculation time is 5 minutes at the tri-blender flow rate of ≥3.0 l/sec. After the complete dissolution, the rinsing is activated; the solution recirculating in the filling line passing through the filters, the filling nozzles and returns to the dissolution tank. The solution is cooling to a temperature of <60° C. When the final control of pH and conductivity is finished and the temperature is lower than the value set, the preparation finishes. Bulk solution is filtered through a pre-filter (3.0 μm pre-filter cartridge) followed by a filtration (0.2 μm sterile filter cartridge). The solution is filled in 100 mL bag and terminally sterilized in autoclave at 121° C. F0=15. The bags are 100% visual inspected and packaged in aluminum overwrap.

Stability of the batch having a midazolam concentration of about 1 mg/ml was determined by accelerated testing at 40° C. for six months. Based on the previous studies, one laboratory batch sterilized at T=121 and F0=20 minutes, with pH value 2.9 pH Units were placed in stability at accelerated condition. The purpose of stability studies was to verify the stability of the formulation. The chemical stability of premix formulation of Midazolam Injection stored under accelerated conditions for six months is show in the graphical representation in FIG. 1-4.

After 6 month of stability at 40° C., there was no observed variation in the pH and in the color of solutions contained in Nexcel bags. A slightly increase of osmolality has been observed during the stability trial. After 6 months at 40° C. there was no observed reduction in Midazolam Assay compared to T=0 sterilized. The total impurities of the formulations packaged in Nexcel bag are still comparable with the results obtained at T=0.

The specification for the finished product having a midazolam concentration of about 1 mg/ml are:

TABLE 2

| | Specifications | | |
|---|---|---|---|
| Test | Limits | Units | Reference Method |
| Description | Then solution must be clear, colourless to light yellow and without visible particles | — | USP <1> |
| Appearance of solution: | | | |
| Clarity | Clear | — | USP <1> |
| Color | NMT Y6 | — | USP <1> |
| Visible particles | Free from visible particles | — | USP <790>/USP <1> |
| Identification HPLC | Same RT of Std | — | USP40 Midazolam Inj. Monograph |
| pH | 2.5-3.5 | pH Units | USP40 Midazolam Inj. Monograph |
| Osmolality | 270-320 | mOsmol/Kg | USP <785> |
| Assay | 90.0-110.0 | % | USP40 Midazolam Inj. Monograph |
| Individual Known impurity | NMT 0.5 | % | USP40 Midazolam Inj. Monograph |
| Individual unknown impurity | NMT 0.1 | | |
| Total impurities | NMT 1.0 | | |
| Assay Chloride | 95.0-105.0 | % | Internal Method |
| Container content | NLT Nominal Volume | mL | USP <697> |
| Weight loss | NMT 2 | % | Internal method |

TABLE 2-continued

| Test | Specifications | | |
|---|---|---|---|
| | Limits | Units | Reference Method |
| Particulate Matter | | | |
| ≥10 micron | NMT 6000 | No. Part/Bag | USP<788> |
| ≥25 micron | NMT 600 | No. Part/Bag | |
| Bacterial Endotoxin | NMT 8.33 | FU/mg | USP <85> |
| Sterility (Parametric Release) | Sterile | — | SOP GEN094/GEN136 |
| Sterility (container integrity) | Confirmed | — | Internal method |
| Residual Solvent | Compliance with USP <467> | — | USP <467> |
| Elemental impurities | Compliance with ICH Q3D | — | USP <232> |

Obviously, numerous modifications and variations of the present invention are possible in light of the above teachings. It is therefore to be understood that within the scope of the appended claims, the invention may be practiced otherwise than as specifically described herein.

The invention claimed is:

1. A ready-to-use terminally sterilized, preservative-free aqueous midazolam solution in an intravenous laminated flexible plastic bag, comprising 0.25 to 1.5 mg/ml of midazolam, sufficient tonicity adjusting agent to provide an osmolality of from 260 and 320 mosm/kg and sufficient acid and optionally a base to provide a pH of from about 2.5 to 3.5 with the remainder water for injection;
wherein:
the tonicity adjusting agent comprises at least one selected from the group consisting of sodium chloride, potassium chloride and calcium chloride;
the acid comprises hydrochloric acid;
the base, if present, comprises sodium hydroxide; and
the midazolam content after accelerated storage at 40° C. for six months is greater than 97%
the intravenous laminated flexible plastic bag comprises from 3 to 7 layers and has an innermost layer comprises an ethylene-vinyl acetate coplymer.

2. The ready-to-use terminally sterilized, preservative-free aqueous midazolam solution of claim 1, wherein the tonicity adjusting agent is sodium chloride in an amount to provide an osmolality of from 260 and 320 mosm/kg.

3. The ready-to-use terminally sterilized, preservative-free aqueous midazolam solution of claim 2, wherein the amount of sodium chloride added is 9 mg/ml.

4. The ready-to-use terminally sterilized, preservative-free aqueous midazolam solution of claim 1 wherein the solution comprises from about 0.5 mg/ml to 1.25 mg/ml of midazolam.

5. The ready-to-use terminally sterilized, preservative-free aqueous midazolam solution of claim 4 wherein the solution comprises about 0.5 mg/ml of midazolam.

6. The ready-to-use terminally sterilized, preservative-free aqueous midazolam solution of claim 4 wherein the solution comprises about 1 mg/ml of midazolam.

7. The ready-to-use terminally sterilized, preservative-free aqueous midazolam solution of claim 1 wherein the pH is 2.5 to 3.5.

8. The ready-to-use terminally sterilized, preservative-free aqueous midazolam solution of claim 7 wherein the is 2.8 to 3.2.

9. The ready-to-use terminally sterilized, preservative-free aqueous midazolam solution of claim 8 wherein the pH is about 3.

10. The ready-to-use terminally sterilized, preservative-free aqueous midazolam solution of claim 1 wherein the midazolam content is about 0.5 mg/ml, the pH is about 3, the tonicity adjusting agent is sodium chloride, and acid is hydrochloric acid.

11. The ready-to-use terminally sterilized, preservative-free aqueous midazolam solution of claim 1 wherein the midazolam content is about 1 mg/ml, the pH is about 3, the tonicity adjusting agent is sodium chloride, and acid is hydrochloric acid.

12. The ready-to-use terminally sterilized, preservative-free aqueous midazolam solution of claim 11 wherein the amount of sodium chloride is about 9 mg/ml of solution.

13. The ready-to-use terminally sterilized, preservative-free aqueous midazolam solution of claim 1, wherein the solution consists essentially of the midazolam, the tonicity agent, water, the acid, and optionally the base.

* * * * *